(12) United States Patent
Kakuda et al.

(10) Patent No.: US 8,513,261 B2
(45) Date of Patent: Aug. 20, 2013

(54) TABLET AND GRANULATED POWDER CONTAINING 6-FLUORO-3-HYDROXY-2-PYRAZINECARBOXAMIDE

(75) Inventors: Sahoe Kakuda, Toyama (JP); Setsuko Nishimura, Toyama (JP); Takafumi Hirota, Toyama (JP)

(73) Assignee: Toyama Chemical Co., Ltd., Tokyo (JP)

( * ) Notice: Subject to any disclaimer, the term of this patent is extended or adjusted under 35 U.S.C. 154(b) by 0 days.

(21) Appl. No.: 13/256,075

(22) PCT Filed: Mar. 12, 2010

(86) PCT No.: PCT/JP2010/054191
§ 371 (c)(1),
(2), (4) Date: Sep. 12, 2011

(87) PCT Pub. No.: WO2010/104170
PCT Pub. Date: Sep. 16, 2010

(65) Prior Publication Data
US 2012/0010221 A1    Jan. 12, 2012

(30) Foreign Application Priority Data
Mar. 13, 2009   (JP) ................. 2009-061837

(51) Int. Cl.
*A61K 31/4965*    (2006.01)
*A61P 31/16*    (2006.01)
*C07D 241/02*    (2006.01)

(52) U.S. Cl.
USPC ................ 514/255.06; 544/406

(58) Field of Classification Search
USPC ................................. 514/255.06
See application file for complete search history.

(56) References Cited

U.S. PATENT DOCUMENTS

| | | | |
|---|---|---|---|
| 5,879,706 A * | 3/1999 | Carter et al. | 424/464 |
| 6,380,381 B1* | 4/2002 | Obara | 536/84 |
| 2002/0013316 A1 | 1/2002 | Furuta et al. | |
| 2004/0034039 A1 | 2/2004 | Nakano et al. | |
| 2011/0028510 A1* | 2/2011 | Altmeyer et al. | 514/300 |

FOREIGN PATENT DOCUMENTS

| | | |
|---|---|---|
| CN | 1313768 A | 9/2001 |
| JP | 9 208468 | 8/1997 |
| JP | 2002 167327 | 6/2002 |
| JP | 2002 173428 | 6/2002 |
| JP | 2007 186470 | 7/2007 |
| WO | 00 10569 | 3/2000 |
| WO | WO 2005/120463 A1 | 12/2005 |

OTHER PUBLICATIONS

Tousey, Pharm Tech, 2002,p. 8-13.*
Office Action issued Aug. 3, 2012, in Chinese Patent Application No. 201080011876.6 with English translation.
Extended European Search Report issued Jun. 18, 2012, in European Patent Application No. 10750921.8.
Oshima, T., et al., "Effect of Size and Shape of Tablets and Capsules on Ease of Grasping and Swallowing (1): Comparison between Elderly and Students," JPN. J. Pharm. Health Care Sci., vol. 32, No. 8, pp. 842-848, (2006) (with English Abstract).
"Development of Pharmaceuticals," K. K. Hirokawa Shoten, vol. 12, First Edition, pp. 178-185, (Oct. 15, 1990).
"Development of Pharmaceuticals," K. K. Hirokawa Shoten, vol. 12, First Edition, pp. 166-167, (Oct. 15, 1990).
International Search Report issued Apr. 20, 2010 in PCT/JP10/054191filed Mar. 12, 2010.

* cited by examiner

*Primary Examiner* — Sreeni Padmanabhan
*Assistant Examiner* — Jason A Deck
(74) *Attorney, Agent, or Firm* — Oblon, Spivak, McClelland, Maier & Neustadt, L.L.P.

(57) ABSTRACT

Disclosed is a useful tablet which contains a high quantity of 6-fluoro-3-hydroxy-2-pyrazinecarboxamide or a salt thereof; has a size that is easy to ingest; has superior release characteristics; and has a hardness that can withstand film coating, packaging, and transportation.

18 Claims, No Drawings

TABLET AND GRANULATED POWDER CONTAINING 6-FLUORO-3-HYDROXY-2-PYRAZINECARBOXAMIDE

TECHNICAL FIELD

The present invention is a tablet containing (1) 6-fluoro-3-hydroxy-2-pyrazinecarboxamide or a salt thereof, (2) a low substituted hydroxypropyl cellulose or croscarmellose sodium and (3) a binder, and relates to the tablet and a granulated powder in which the amount of 6-fluoro-3-hydroxy-2-pyrazinecarboxamide or a salt thereof contained therein is 50 to 95% of the mass of the tablet or the granulated powder.

BACKGROUND ART

6-Fluoro-3-hydroxy-2-pyrazinecarboxamide (hereinafter, it will be referred to as the compound A) or a salt thereof is a compound which is useful as a treatment such as prevention or therapy of a viral infection or, particularly, an influenza viral infection [Patent Document 1].

One to several tablet(s) containing the compound A or a salt thereof is/are administered per os. For improving the drug compliance, there has been a demand for a tablet where numbers of tablets to be administered are reduced and ingestion thereof is easy. Thus, there has been a demand for a development of a tablet where the amount of the compound A or a salt thereof contained therein is high and the size of the tablet is in a size of being able to be easily ingested.

There has been also a demand for a mixed powder for tableting for the manufacture of the tablet as such.

In the manufacture of tablets, it is essential that the mixed powder for tableting has a compression molding property. When the compression molding property of the mixed powder for tableting is low, hardness of the tablet becomes low. In that case, there is a possibility that the tablets are broken upon packaging or during transportation or that the tablets are worn away or cracked in a coating machine upon subjecting the tablets to film coating.

On the other hand, when the cohesive force of the mixed powder for tableting is strong, fluidity is poor and it is difficult to provide a predetermined amount of the mixed powder for tableting to a mortar upon tableting. Therefore, discrepancies in the tablet masses become large and quality is deteriorated.

It has been reported already that the size of an easily ingestible circular tablet has a diameter of 7 to 8 mm and that the size of an easily ingestible elliptic tablet has a long diameter of 9 mm [Non-Patent Document 1]. A tablet in a big size is hardly ingestible due to the resisting feel and the compressive feel not only for small children and patients having a difficulty in swallowing but also for ordinary adult patients, and causing the lowering of the drug compliance. Size of a tablet is preferred to be not larger than 9 mm.

The compound A or a salt thereof has such a property that no compressive molding property is available, specific volume is big, cohesive force is strong and fluidity is low. It is difficult that a tablet containing a large amount of the compound A or a salt thereof and being in an easily ingestible size is manufactured by a conventional method.

There has been reported a method where an additive having a high molding property such as crystalline cellulose is compounded to manufacture a mixed powder for tableting having a high compressive molding property whereby a tablet having a necessary hardness is prepared [Non-Patent Document 2].

However, in order to manufacture a tablet containing the compound A or a salt thereof where the necessary hardness is available, it is necessary that the amount of the additive contained therein is not less than 50% or, preferably, not less than 60% of the mass of the tablet. Due to such a reason, the size of a tablet becomes big.

As to a method where the cohesive force of the mixed powder for tableting is lowered and the fluidity is enhanced, there has been reported a method where a fluidity promoter is compounded [Non-Patent Document 3].

However, it is not possible to improve the cohesive force of the compound A or a salt thereof only by means of compounding a fluidity promoter. The mixed powder for tableting having poor fluidity shows a poor charging property into a mortar upon tableting. Therefore, discrepancies in the tablet masses become big and quality is deteriorated.

On the other hand, there has been known a method in which a binder is used and granulation is carried out by means of a dry or a wet granulation method whereby the bonding strength among the particles upon tableting is enhanced. However, although the necessary hardness is achieved by this method, the dissolution property lowers due to the rise in the bonding strength among the particles.

Up to now, there has been known no tablet in which the amount of the compound A or a salt thereof contained therein is high, the size is an easily ingestible size, the dissolution property is excellent and the hardness is durable against film coating, packaging and transportation whereby the tablet is stable for a long period of time.

PRIOR ART DOCUMENTS

Patent Document

Patent Document 1: Pamphlet of the International Publication WO 00/10569

Non-Patent Documents

Non-Patent Document 1: Iryo Yakugaku (=Jpn. J. Pharm. Health Care Sci.), Volume 32, pages 842 to 848, 2006

Non-Patent Document 2: "Development of Pharmaceuticals" edited by Hisashi Ichibangase and two others, Volume 12, First Edition, published by K. K. Hirokawa Shoten, Volume 12, published on Oct. 15, 1990, pages 178 to 185

Non-Patent Document 3: "Development of Pharmaceuticals" edited by Hisashi Ichibangase and two others, Volume 12, First Edition, published by K. K. Hirokawa Shoten, Volume 12, published on Oct. 15, 1990, pages 166 to 167

SUMMARY OF THE INVENTION

Problem to be Solved by the Invention

There has been a demand for a tablet in which the amount of the compound A or a salt thereof contained therein is high, the size is an easily ingestible size, the dissolution property is excellent and the hardness is durable against film coating, packaging and transportation whereby the tablet is stable for a long period of time and also for a mixed powder for tableting for the manufacture of the tablet as such.

Means for Solving the Problems

Under such circumstances, the present inventors have repeatedly carried out intensive studies and, as a result, they have found a tablet in which the amount of the compound A or a salt thereof contained therein is high, the size is an easily ingestible size, the dissolution property is excellent and the hardness is durable against film coating, packaging and transportation whereby the tablet is stable for a long period of time.

They have further found a mixed powder for tableting being excellent as an intermediate product for the manufacture of the tablet as such and also found a granulated powder being excellent for the manufacture of the mixed powder for tableting whereupon the present invention has been achieved.

Advantages of the Invention

The tablet of the present invention is a tablet containing (1) the compound A or a salt thereof, (2) a low substituted hydroxypropyl cellulose or croscarmellose sodium and (3) a binder, wherein the amount of the compound A or a salt thereof contained therein is 50 to 95% of the mass of the tablet.

In the tablet of the present invention, the amount of the compound A or a salt thereof contained therein is high, the size is an easily ingestible size, the dissolution property is excellent and the hardness is durable against film coating, packaging and transportation.

The tablet of the present invention is useful as a tablet containing a high amount of the compound A or a salt thereof.

The granulated powder of the present invention is a granulated powder containing (1) the compound A or a salt thereof, (2) a low substituted hydroxypropyl cellulose or croscarmellose sodium and (3) a binder, wherein the amount of the compound A or a salt thereof contained therein is 50 to 95% of the mass of the granulated powder.

The granulated powder of the present invention contains a high amount of the compound A or a salt thereof and is useful as a granulated powder for the manufacture of a tablet containing a high amount of the compound A or a salt thereof.

MODE FOR CARRYING OUT THE INVENTION

The present invention will now be more specifically illustrated as hereunder.

The term % used in this specification means the percentage by mass unless otherwise stipulated.

The compound A or a salt thereof used in the present invention is able to be produced by a process mentioned, for example, in the pamphlet of the international publication WO 00/10569.

The amount of the compound A or a salt thereof contained therein may be 50 to 95%, preferably 60 to 90% or, more preferably, 70 to 85% of the mass of the tablet or the granulated powder.

The low substituted hydroxypropyl cellulose or croscarmellose sodium used in the present invention is able to be compounded in the inside and/or the outside of the granulated powder.

The amount of the low substituted hydroxypropyl cellulose or croscarmellose sodium contained therein may be 2 to 20%, preferably 2.5 to 15% or, more preferably, 5 to 10% of the mass of the tablet.

The low substituted hydroxypropyl cellulose is preferred.

There is no particular limitation for the binder used in the present invention and examples thereof include povidone, hydroxypropyl cellulose, hypromellose, carmellose sodium, methyl cellulose, polyvinyl alcohol, gum arabic and dextrin. One of those binders may be used or two or more thereof may be used in combination.

As to a preferred binder, povidone may be exemplified.

Examples of the povidone include povidone K 17, povidone K 25, povidone K 30 and povidone K 90.

The amount of the povidone contained therein may be 1 to 20% or, preferably, 2.5 to 10% of the mass of the tablet or the granulated powder.

It is preferred that a lubricant is added to the tablet and to the granulated powder of the present invention.

Examples of the lubricant which is used in the present invention upon necessity include sodium stearyl fumarate, stearic acid, magnesium stearate, calcium stearate, talc and sucrose fatty acid ester.

Examples of the preferred lubricant include sodium stearyl fumarate and talc and the more preferred one is sodium stearyl fumarate.

The amount of the lubricant contained therein is 0.1 to 5%, preferably 0.2 to 2% or, more preferably, 0.2 to 1% of the mass of the tablet or the granulated powder.

It is preferred that silicon dioxide is added to the tablet and to the granulated powder of the present invention.

Examples of the silicon dioxide which is used in the present invention upon necessity include hydrated silicon dioxide and light anhydrous silicic acid.

The amount of the silicon dioxide contained therein is 0.5 to 15%, preferably 2 to 10% or, more preferably 3 to 5% of the mass of the tablet or the granulated powder.

It is also possible that a disintegrating agent is further added to the tablet and to the granulated powder of the present invention upon necessity.

There is no particular limitation for the disintegrating agent used in the present invention upon necessity and examples thereof include carmellose, carmellose calcium, carboxymethyl starch sodium, crospovidone and partly pregelatinized starch. With regard to the disintegrating agents, one of them may be used or two or more thereof may be used in combination. Crospovidone is preferred.

The disintegrating agent may be compounded in the inside and/or the outside of the granulated powder.

The particle size of crospovidone is preferred to be 100 μm or smaller. When crospovidone of which the particle size is more than 100 μm is used, there may be the case in which small convex projections are found on the surface of the tablet with elapse of time. In addition, when crospovidone having a small particle size is used, its dissolution property is much more improved.

The amount of crospovidone contained therein may be 1 to 10% or, preferably 2 to 5% of the mass of the tablet or the granulated powder.

An excipient may be further added to the tablet and the granulated powder of the present invention.

Examples of the excipient used in the present invention upon necessity include sugar alcohol such as erythritol, mannitol, xylitol and sorbitol; saccharide such as sucrose, powdery sugar, lactose and glucose; cyclodextrin such as α-cyclodextrin, β-cyclodextrin, γ-cyclodextrin, hydroxypropyl β-cyclodextrin and sulfobutyl ether β-cyclodextrin; cellulose such as crystalline cellulose and microcrystalline cellulose; and starch such as corn starch, potato starch and partly pregelatinized starch. With regard to those excipients, one of them may be added or two or more thereof may be added in combination.

There is no particular limitation for the adding amount of the excipient but a necessary amount depending upon the object may be appropriately compounded therewith.

In the tablet and the granulated powder of the present invention, an additive which has been commonly used in pharmaceuticals may be used within such a range that the effect of the present invention is not deteriorated thereby.

Examples of the additive include a corrigent, a coloring agent, a flavoring agent, a surfactant, a coating agent and a plasticizer.

Examples of the corrigent include aspartame, saccharine, stevia, thaumatin and acesulfame potassium.

Examples of the coloring agent include titanium dioxide, red ferric oxide, yellow ferric oxide, black iron oxide, edible Red No. 102, edible Yellow No. 4 and edible Yellow No. 5.

Examples of the flavoring agent include essential oils such as orange oil, lemon oil, peppermint oil and pineapple oil; essence such as orange essence and peppermint essence; flavors such as cherry flavor, vanilla flavor and fruit flavor; powdery flavors such as yogurt micron, apple micron, banana micron, peach micron, strawberry micron and orange micron; vanillin; and ethyl vanillin.

Examples of the surfactant include sodium lauryl sulfate, sodium dioctyl sulfosuccinate, polysorbate and polyoxyethylene hydrogenated castor oil.

Examples of the coating agent include hypromellose, aminoalkyl methacrylate copolymer E, aminoalkyl methacrylate copolymer RS, ethyl cellulose, cellulose acetate phthalate, hydroxypropyl methyl cellulose phthalate, methacrylic acid copolymer L, methacrylic acid copolymer LD and methacrylic acid copolymer S, polyvinyl alcohol and hydroxypropyl methyl cellulose acetate succinate.

Examples of the plasticizer include triethyl citrate, Macrogol, triacetin and propylene glycol.

With regard to these additives as such, one of them may be used or two or more thereof may be used in combination. There is no particular limitation for the compounding amount thereof but the additives may be appropriately compounded depending upon the object so that the effect is well achieved.

In administering the tablet of the present invention, method, dose and frequency thereof are able to be appropriately selected depending upon age, body weight and symptom of the patient and, usually, the dose by which the pharmaceutical effect is able to be achieved may be administered either once daily or several times in installments a day. Usually, 10 to 5,000 mg or, preferably 200 to 2,400 mg as the compound A may be administered per day to an adult once or several times in installments.

With regard to a method for the manufacture of the tablet of the present invention, there may be exemplified a method in which a granulated powder is manufactured by a dry or a wet granulation method followed, if necessary, by adding an excipient, a disintegrating agent and/or a lubricant thereto and the resulting mixed powder for tableting is made into tablets.

In the method for the manufacture of the granulated powder of the present invention, a wet granulation method may be exemplified as a preferred granulation method.

Examples of the wet granulation method include a fluidized bed granulation method, a centrifugal tumbling granulation method, a mixing/stirring granulation method, a high-speed mixing/stirring granulation method, a tumbling granulation method, a wet crushing granulation method and an extruding granulation method.

Examples of the preferred wet granulation method include a fluidized bed granulation method, a centrifugal tumbling granulation method, a mixing/stirring granulation method, a high-speed mixing/stirring granulation method, a tumbling granulation method and a wet crushing granulation method and, among them, a fluidized bed granulation method is more preferred. When a fluidized bed granulation method is adopted, a granulated powder having high bulkiness is prepared and, as compared with other granulation methods, a granulated powder having a high compressive molding property is apt to be prepared.

Examples of the method for adding the binder during the granulation include (1) a method in which a binder dissolved in water is sprayed onto a mixed powder comprising the compound A or a salt thereof, a disintegrating agent, etc. and (2) a method in which water is sprayed onto a mixture of the compound A or a salt thereof, a disintegrating agent and a binder.

Examples of addition of silicon dioxide include (1) a method in which powdery silicon dioxide is added to a mixed powder comprising the compound A or a salt thereof, a disintegrating agent, etc. and (2) a method in which silicon dioxide and a binder are dispersed in water and then sprayed onto a mixed powder. The method (2) is a preferred adding method since the compressive molding property and the dissolution property upon making into tablets are improved therein as compared with the method (1).

Usefulness of the tablet of the present invention will now be illustrated by way of the following Test Examples.

Test Example 1

With regard to the samples, there were used the uncoated plain tablets of Examples 1 and 19 and Comparative Examples 1, 2 and 3 and the uncoated plain tablets as well as their film-coated tablets of Examples 2 and 3 and Comparative Examples 4 and 5.

In the measurement of the hardness, there was used a portable checker PC 30 (Okada Seiko) or an automatic measuring device for tablet characteristics TM 3-3 (Kikusui Seisakusho).

The dissolution test was conducted by a puddle method for a dissolution test according to the Japanese Pharmacopoeia. Revolutions of the puddle were made 50 rpm. A sample was poured into 900 mL of an acetate buffer (pH 4.5) followed by stirring for 15 minutes. The test solution was collected and the dissolution rate (%) of the compound A was determined by means of an absorbance method.

In the measurement of the hardness, core tablets were used at all times. In the dissolution test, core tablets of Examples 1 and 19 and Comparative Examples 1, 2 and 3 and film coated tablets of Examples 2 and 3 and Comparative Examples 4 and 5 were used. The result is shown in Table 1.

TABLE 1

|  | Ex 1 | Ex 2 | Ex 3 | Ex 19 | CE 1 | CE 2 | CE 3 | CE 4 | CE 5 |
|---|---|---|---|---|---|---|---|---|---|
| Compound A | 210.0 | 205.3 | 223.5 | 242.3 | 250.0 | 236.2 | 224.2 | 216.3 | 223.5 |
| Low substituted Hydroxypropyl Cellulose | 26.3 | 25.6 | 0.0 | 5.5 | 0.0 | 0.0 | 0.0 | 0.0 | 0.0 |
| Croscarmellose Sodium | 0.0 | 0.0 | 5.6 | 0.0 | 0.0 | 0.0 | 0.0 | 0.0 | 0.0 |
| Crospovidone | 0.0 | 0.0 | 0.0 | 0.0 | 0.0 | 0.0 | 0.0 | 13.5 | 0.0 |
| Carboxymethyl Starch Sodium | 0.0 | 0.0 | 0.0 | 0.0 | 0.0 | 0.0 | 0.0 | 0.0 | 5.6 |
| Povidone K 30 | 12.4 | 12.8 | 14.0 | 4.2 | 0.0 | 12.5 | 12.3 | 13.5 | 14.0 |
| Silicon Dioxide | 0.0 | 5.1 | 5.6 | 2.4 | 0.0 | 0.0 | 12.3 | 5.4 | 5.6 |

TABLE 1-continued

|  | Ex 1 | Ex 2 | Ex 3 | Ex 19 | CE 1 | CE 2 | CE 3 | CE 4 | CE 5 |
|---|---|---|---|---|---|---|---|---|---|
| Sodium Stearyl Fumarate | 1.3 | 1.2 | 1.3 | 0.6 | 0.0 | 1.3 | 1.2 | 1.3 | 1.3 |
| Opadry | 0.0 | 10.0 | 10.0 | 0.0 | 0.0 | 0.0 | 0.0 | 10.0 | 10.0 |
| Total Mass (mg) | 250.0 | 260.0 | 260.0 | 255.0 | 250.0 | 250.0 | 250.0 | 260.0 | 260.0 |
| Hardness (N) | 87 | 81 | 121 | 53 | MI | 83 | 66 | 113 | 109 |
| Dissolution Rate (%) | 91.3 | 93.5 | 86.7 | 93.9 | MI | 5.3 | 4.5 | 76.3 | 63.6 |

CE: Comparative Example
MI: Measurement impossible

The preparation (Comparative Example 1) using neither binders nor disintegrating agents was unable to be made into tablets whereby the measurement of the tablet hardness and the dissolution rate was not possible.

The preparations (Comparative Examples 2 and 3) using no disintegrating agent showed a very low dissolution property.

In the preparations (Comparative Examples 4 and 5) using crospovidone or carboxymethyl starch sodium as a disintegrating agent, their dissolution rate after 15 minutes was as low as not higher than 85%.

On the contrary, in the preparations (Examples 1, 2 and 19) using a low substituted hydroxypropyl cellulose as a disintegrating agent and in the preparation (Example 3) using croscarmellose sodium as a disintegrating agent, their dissolution rate after 15 minutes was as excellent as not lower than 85%.

The tablets in which the compound A, povidone K 30 and low substituted hydroxypropyl cellulose or croscarmellose sodium were compounded were excellent as the tablets where high amount of the compound A was contained therein and excellent dissolution property and necessary hardness were available.

Test Example 2

As to the samples, there were used uncoated plain tablets and their film-coated tablets of Examples 4 to 10 and core tablet of Example 11.

Measurement of the hardness and the dissolution test were carried out in the same manner as in Test Example 1.

For the measurement of the hardness, core tablets were used at all times. For the dissolution test, there were used core tablet of Example 11 and film-coated tablets of Examples 4 to 10. The result is shown in Table 2.

TABLE 2

|  | Ex 4 | Ex 5 | Ex 6 | Ex 7 | Ex 8 | Ex 9 | Ex 10 | Ex 11 |
|---|---|---|---|---|---|---|---|---|
| Compound A | 200.0 | 200.0 | 200.0 | 200.0 | 200.0 | 200.0 | 200.0 | 209.4 |
| Low substituted Hydroxypropyl Cellulose | 25.0 | 25.0 | 25.0 | 25.0 | 25.0 | 25.0 | 25.0 | 26.2 |
| Povidone K 30 | 12.5 | 0.0 | 0.0 | 0.0 | 0.0 | 0.0 | 0.0 | 13.1 |
| Polyvinyl Alcohol | 0.0 | 12.5 | 0.0 | 0.0 | 0.0 | 0.0 | 0.0 | 0.0 |
| Hypromellose 2910 | 0.0 | 0.0 | 12.5 | 0.0 | 0.0 | 0.0 | 0.0 | 0.0 |
| Hydroxypropyl Cellulose (HPC-L) | 0.0 | 0.0 | 0.0 | 12.5 | 0.0 | 0.0 | 0.0 | 0.0 |
| Hydroxypropyl Cellulose (HPC-SSL) | 0.0 | 0.0 | 0.0 | 0.0 | 12.5 | 0.0 | 0.0 | 0.0 |
| Methyl Cellulose | 0.0 | 0.0 | 0.0 | 0.0 | 0.0 | 12.5 | 0.0 | 0.0 |
| Gum Arabic | 0.0 | 0.0 | 0.0 | 0.0 | 0.0 | 0.0 | 12.5 | 0.0 |
| Silicon Dioxide | 12.5 | 12.5 | 12.5 | 12.5 | 12.5 | 12.5 | 12.5 | 0.0 |
| Sodium Stearyl Fumarate | 0.5 | 0.5 | 0.5 | 0.5 | 0.5 | 0.5 | 0.5 | 1.3 |
| Opadry | 7.5 | 7.5 | 7.5 | 7.5 | 7.5 | 7.5 | 7.5 | 0.0 |
| Total Mass (mg) | 258.0 | 258.0 | 258.0 | 258.0 | 258.0 | 258.0 | 258.0 | 250.0 |
| Hardness (N) | 94 | 82 | 75 | 72 | 72 | 75 | 69 | 74 |
| Dissolution Rate (%) | 95.1 | 99.7 | 99.7 | 96.3 | 98.4 | 99.0 | 98.9 | 91.5 |

In the preparations (Examples 4 to 11) using povidone K 30, polyvinyl alcohol, hypromellose 2910, hydroxypropyl cellulose, methyl cellulose and gum arabic as a binder, their dissolution rates after 15 minutes were as excellent as not lower than 90%.

The tablets in which the compound A, a binder and a low substituted hydroxypropyl cellulose were compounded were excellent as the tablets where high amount of the compound A was contained therein and excellent dissolution property and necessary hardness were available.

Test Example 3

The core tablets of Examples 11 to 16 were used as test samples.

Measurement of the hardness of core tablets and the dissolution tests thereof was carried out in the same manner as in Test Example 1. The result is shown in Table 3.

TABLE 3

|  | Ex 11 | Ex 12 | Ex 13 | Ex 14 | Ex 15 | Ex 16 |
|---|---|---|---|---|---|---|
| Compound A | 209.4 | 207.3 | 205.3 | 203.1 | 199.0 | 189.1 |
| Low substituted Hydroxypropyl Cellulose | 26.2 | 25.9 | 25.6 | 25.4 | 24.9 | 23.6 |
| Povidone K 30 | 13.1 | 13.0 | 12.8 | 12.7 | 12.4 | 12.5 |
| Silicon Dioxide | 0.0 | 2.6 | 5.1 | 7.6 | 12.4 | 23.6 |
| Sodium Stearyl Fumarate | 1.3 | 1.2 | 1.2 | 1.2 | 1.3 | 1.2 |
| Total Mass (mg) | 250.0 | 250.0 | 250.0 | 250.0 | 250.0 | 250.0 |
| Hardness (N) | 74 | 75 | 75 | 82 | 78 | 85 |
| Dissolution Rate (%) | 91.5 | 90.8 | 93.5 | 97.1 | 99.6 | 98.9 |

Any of the above tablets showed excellent dissolution property. The tablets (Examples 13 to 16) containing not less than 2% of silicon dioxide showed far better dissolution property and the tablets (Examples 14 to 16) containing not less than 3% of silicon dioxide showed still far better dissolution property.

The tablets in which the compound A, povidone K, low substituted hydroxypropyl cellulose and silicon dioxide were compounded were excellent as the tablets where high amount of the compound A was contained therein and excellent dissolution property and necessary hardness were available.

Test Example 4

The core tablets and the film coated tablets thereof manufactured in Examples 17 and 18 were used as test samples.

Measurement of the hardness of the core tablets and the dissolution tests of the film coated tablets were carried out in the same manner as in Test Example 1. The result is shown in Table 4.

TABLE 4

|  | Example 17 | Example 18 |
|---|---|---|
| Compound A | 200.0 | 200.0 |
| Low substituted Hydroxypropyl Cellulose | 26.2 | 25.0 |
| Povidone K 30 | 11.5 | 12.5 |
| Silicon Dioxide | 11.5 | 12.5 |
| Crospovidone | 5.3 | 0.0 |
| Sodium Stearyl Fumarate | 0.5 | 0.5 |
| Opadry | 8.0 | 10.0 |
| Total Mass (mg) | 263.0 | 260.5 |
| Hardness (N) | 61 | 46 |
| Dissolution Rate (%) | 96.9 | 91.1 |

Any of the tablet manufactured by a fluidized bed granulation method which is a wet granulation method (Example 17) and the tablet manufactured by a high-speed mixing/stirring granulation method (Example 18) showed excellent dissolution property and they were excellent as the tablets.

EXAMPLES

The present invention will now be illustrated by way of the following Examples and Comparative Examples although the present invention is not limited thereto.

The compound A was used after finely ground.

As to a coating agent, there was used Opadry 03A42214 (containing 79.25% of hypromellose 2910, 10% of titanium oxide, 10% of talc and 0.75% of yellow iron sesquioxide; manufactured by Nippon Colorcon).

Conditions for tableting in each of Examples and Comparative Examples were 8.5 mm DR of a punch and 10 kN of tableting pressure unless otherwise mentioned.

Example 1

The compound A (6 g) and 0.75 g of a low substituted hydroxypropyl cellulose (L-HPC LH-11, manufactured by Shin Etsu Chemical) were mixed in a mortar. To this mixed powder was added 1.75 g of a 20% aqueous solution of povidone K 30 (Plasdone K 29/32, manufactured by International Specialty Products) followed by granulating. The resulting granulated powder was dried overnight at 40° C. The resulting granulated powder was passed through a sieve having an opening size of 500 μm and sodium stearyl fumarate (PRUV, manufactured by JRS Pharma) in an amount corresponding to 0.5% was added to the resulting powder followed by mixing and tableting to give core tablets each weighing 250 mg.

Example 2

The compound A (5 g), 0.63 g of a low substituted hydroxypropyl cellulose (L-HPC LH-B1, manufactured by Shin Etsu Chemical) and 0.13 g of silicon dioxide (Aerosil 200, manufactured by Nippon Aerosil) were mixed in a mortar. To this mixed powder was added 1.55 g of a 20% aqueous solution of povidone K 30 (Plasdone K 29/32, manufactured by International Specialty Products) followed by granulating. The resulting granulated powder was dried overnight at 40° C. The resulting granulated powder was passed through a sieve having an opening size of 500 μm and sodium stearyl fumarate (PRUV, manufactured by JRS Pharma) in an amount corresponding to 0.5% was added to the resulting powder followed by mixing and tableting to give core tablets each weighing 250 mg. The core tablet was coated with 10 mg of a coating agent to give a film-coated tablet.

Example 3

The compound A (5 g), 0.13 g of croscarmellose sodium (Ac-Di-Sol, manufactured by FMC BioPolymer) and 0.13 g of silicon dioxide (Aerosil 200, manufactured by Nippon Aerosil) were mixed in a mortar. To this mixed powder was added 1.55 g of a 20% aqueous solution of povidone K 30 (Plasdone K 29/32, manufactured by International Specialty Products) followed by granulating. The resulting granulated powder was dried overnight at 40° C. The resulting granulated powder was passed through a sieve having an opening size of 500 μm and sodium stearyl fumarate (PRUV, manufactured by JRS Pharma) in an amount corresponding to 0.5% was added to the resulting powder followed by mixing and tableting to give core tablets each weighing 250 mg. The core tablet was coated with 10 mg of a coating agent to give a film-coated tablet.

Example 4

The compound A (6 g), 0.75 g of a low substituted hydroxypropyl cellulose (L-HPC LH-11, manufactured by Shin Etsu Chemical), 0.375 g of silicon dioxide (Aerosil 200, manufactured by Nippon Aerosil) and 0.375 g of povidone K 30 (Plasdone K29/32, manufactured by International Specialty Product) were mixed in a mortar. To this mixed powder was added 1.67 g of pure water followed by granulating. The resulting granulated powder was dried overnight at 40° C. The resulting granulated powder was passed through a sieve having an opening size of 500 μm and sodium stearyl fumarate (PRUV, manufactured by JRS Pharma) in an amount corresponding to 0.2% was added to the resulting powder followed by mixing and tableting to give core tablets each weighing 250.5 mg. The core tablet was coated with 7.5 mg of a coating agent to give a film-coated tablet.

Example 5

The compound A (6 g), 0.75 g of a low substituted hydroxypropyl cellulose (L-HPC LH-11, manufactured by Shin Etsu Chemical) and 0.375 g of silicon dioxide (Aerosil 200, manufactured by Nippon Aerosil) were mixed in a mortar. To this mixed powder was added 1.86 g of a 20% aqueous solution of polyvinyl alcohol (Gohsenol EG-05, manufactured by Nippon Synthetic Chemical Industry) followed by granulating. The resulting granulated powder was dried overnight at 40° C. The resulting granulated powder was passed through a sieve having an opening size of 500 μm and sodium stearyl fumarate (PRUV, manufactured by JRS Pharma) in an amount corresponding to 0.2% was added to the resulting powder followed by mixing and tableting to give core tablets each weighing 250.5 mg. The core tablet was coated with 7.5 mg of a coating agent to give a film-coated tablet.

Example 6

The compound A (6 g), 0.75 g of a low substituted hydroxypropyl cellulose (L-HPC LH-11, manufactured by Shin Etsu Chemical), 0.375 g of silicon dioxide (Aerosil 200, manufactured by Nippon Aerosil) and 0.375 g of hypromellose 2910 (TC-5RW, manufactured by Shin Etsu Chemical) were mixed in a mortar. To this mixed powder was added 1.85 g of pure water followed by granulating. The resulting granulated powder was dried overnight at 40° C. The resulting granulated powder was passed through a sieve having an opening size of 500 μm and sodium stearyl fumarate (PRUV, manufactured by JRS Pharma) in an amount corresponding to 0.2% was added to the resulting powder followed by mixing and tableting to give core tablets each weighing 250.5 mg. The core tablet was coated with 7.5 mg of a coating agent to give a film-coated tablet.

Example 7

The compound A (6 g), 0.75 g of a low substituted hydroxypropyl cellulose (L-HPC LH-11, manufactured by Shin Etsu Chemical), 0.375 g of silicon dioxide (Aerosil 200, manufactured by Nippon Aerosil) and 0.375 g of hydroxypropyl cellulose (HPC-L, manufactured by Nippon Soda) were mixed in a mortar. To this mixed powder was added 1.92 g of pure water followed by granulating. The resulting granulated powder was dried overnight at 40° C. The resulting granulated powder was passed through a sieve having an opening size of 500 μm and sodium stearyl fumarate (PRUV, manufactured by JRS Pharma) in an amount corresponding to 0.2% was added to the resulting powder followed by mixing and tableting to give core tablets each weighing 250.5 mg. The core tablet was coated with 7.5 mg of a coating agent to give a film-coated tablet.

Example 8

The compound A (6 g), 0.75 g of a low substituted hydroxypropyl cellulose (L-HPC LH-11, manufactured by Shin Etsu Chemical), 0.375 g of silicon dioxide (Aerosil 200, manufactured by Nippon Aerosil) and 0.375 g of hydroxypropyl cellulose (HPC-SSL, manufactured by Nippon Soda) were mixed in a mortar. To this mixed powder was added 2.0 g of pure water followed by granulating. The resulting granulated powder was dried overnight at 40° C. The resulting granulated powder was passed through a sieve having an opening size of 500 μm and sodium stearyl fumarate (PRUV, manufactured by JRS Pharma) in an amount corresponding to 0.2% was added to the resulting powder followed by mixing and tableting to give core tablets each weighing 250.5 mg. The core tablet was coated with 7.5 mg of a coating agent to give a film-coated tablet.

Example 9

The compound A (6 g), 0.75 g of a low substituted hydroxypropyl cellulose (L-HPC LH-11, manufacture by Shin Etsu Chemical), 0.375 g of silicon dioxide (Aerosil 200, manufactured by Nippon Aerosil) and 0.375 g of methyl cellulose (Metolose SM-4, manufactured by Shin Etsu Chemical) were mixed in a mortar. To this mixed powder was added 2.08 g of pure water followed by granulating. The resulting granulated powder was dried overnight at 40° C. The resulting granulated powder was passed through a sieve having an opening size of 500 μm and sodium stearyl fumarate (PRUV, manufactured by JRS Pharma) in an amount corresponding to 0.2% was added to the resulting powder followed by mixing and tableting to give core tablets each weighing 250.5 mg. The core tablet was coated with 7.5 mg of a coating agent to give a film-coated tablet.

Example 10

The compound A (6 g), 0.75 g of a low substituted hydroxypropyl cellulose (L-HPC LH-11, manufactured by Shin Etsu Chemical), 0.375 g of silicon dioxide (Aerosil 200, manufactured by Nippon Aerosil) and 0.375 g of powdered acacia (manufactured by Wako Pure Chemical Industries) were mixed in a mortar. To this mixed powder was added 2.07 g of pure water followed by granulating. The resulting granulated powder was dried overnight at 40° C. The resulting granulated powder was passed through a sieve having an opening size of 500 μm and sodium stearyl fumarate (PRUV, manufactured by JRS Pharma) in an amount corresponding to 0.2% was added to the resulting powder followed by mixing and tableting to give core tablets each weighing 250.5 mg. The core tablet was coated with 7.5 mg of a coating agent to give a film-coated tablet.

Example 11

The compound A (30 g) and 3.75 g of a low substituted hydroxypropyl cellulose (L-HPC LH-B1, manufactured by Shin Etsu Chemical) were mixed in a mortar. To this mixed powder was added 9.49 g of a 20% aqueous solution of povidone K 30 (Plasdone K29/32, manufactured by International Specialty Products) followed by granulating. The resulting granulated powder was dried overnight at 40° C. The resulting granulated powder was passed through a sieve having an opening size of 500 μm and sodium stearyl fumarate (PRUV, manufactured by JRS Pharma) in an amount corresponding to 0.5% was added to the resulting powder followed by mixing and tableting to give core tablets each weighing 250 mg.

Example 12

The compound A (5 g), 0.63 g of a low substituted hydroxypropyl cellulose (L-HPC LH-B1, manufactured by Shin Etsu Chemical) and 0.06 g of silicon dioxide (Aerosil 200, manufactured by Nippon Aerosil) were mixed in a mortar. To this mixed powder was added 1.55 g of a 20% aqueous solution of povidone K 30 (Plasdone K29/32, manufactured by International Specialty Products) followed by granulating. The resulting granulated powder was dried overnight at 40° C. The resulting granulated powder was passed through a sieve having an opening size of 500 μm and sodium stearyl fumarate (PRUV, manufactured by JRS Pharma) in an amount corresponding to 0.5% was added to the resulting powder followed by mixing and tableting to give core tablets each weighing 250 mg.

Example 13

The compound A (5 g), 0.63 g of a low substituted hydroxypropyl cellulose (L-HPC LH-B1, manufactured by Shin Etsu Chemical) and 0.13 g of silicon dioxide (Aerosil 200, manufactured by Nippon Aerosil) were mixed in a mortar. To this mixed powder was added 1.56 g of a 20% aqueous solution of povidone K 30 (Plasdone K29/32, manufactured by International Specialty Products) followed by granulating. The resulting granulated powder was dried overnight at 40° C. The resulting granulated powder was passed through a sieve having an opening size of 500 μm and sodium stearyl fumarate (PRUV, manufactured by JRS Pharma) in an amount corresponding to 0.5% was added to the resulting powder followed by mixing and tableting to give core tablets each weighing 250 mg.

Example 14

The compound A (5 g), 0.63 g of a low substituted hydroxypropyl cellulose (L-HPC LH-B1, manufactured by Shin Etsu Chemical) and 0.19 g of silicon dioxide (Aerosil 200, manufactured by Nippon Aerosil) were mixed in a mortar. To this mixed powder was added 1.55 g of a 20% aqueous solution of povidone K 30 (Plasdone K29/32, manufactured by International Specialty Products) followed by granulating. The resulting granulated powder was dried overnight at 40° C. The resulting granulated powder was passed through a sieve having an opening size of 500 μm and sodium stearyl fumarate (PRUV, manufactured by as Pharma) in an amount corresponding to 0.5% was added to the resulting powder followed by mixing and tableting to give core tablets each weighing 250 mg.

Example 15

The compound A (5 g), 0.63 g of a low substituted hydroxypropyl cellulose (L-HPC LH-B1, manufactured by Shin Etsu Chemical) and 0.31 g of silicon dioxide (Aerosil 200, manufactured by Nippon Aerosil) were mixed in a mortar. To this mixed powder was added 1.55 g of a 20% aqueous solution of povidone K 30 (Plasdone K29/32, manufactured by International Specialty Products) followed by granulating. The resulting granulated powder was dried overnight at 40° C. The resulting granulated powder was passed through a sieve having an opening size of 500 μm and sodium stearyl fumarate (PRUV, manufactured by JRS Pharma) in an amount corresponding to 0.5% was added to the resulting powder followed by mixing and tableting to give core tablets each weighing 250 mg.

Example 16

The compound A (6 g), 0.75 g of a low substituted hydroxypropyl cellulose (L-HPC LH-B1, manufactured by Shin Etsu Chemical) and 0.75 g of silicon dioxide (Aerosil 200, manufactured by Nippon Aerosil) were mixed in a mortar. To this mixed powder was added 2.01 g of a 20% aqueous solution of povidone K 30 (Plasdone K29/32, manufactured by International Specialty Products) followed by granulating. The resulting granulated powder was dried overnight at 40° C. The resulting granulated powder was passed through a sieve having an opening size of 500 μm and sodium stearyl fumarate (PRUV, manufactured by JRS Pharma) in an amount corresponding to 0.5% was added to the resulting powder followed by mixing and tableting to give core tablets each weighing 250 mg.

Example 17

Povidone K 30 (Plasdone K29/32, manufactured by International Specialty Products) (430 g) was added to and dissolved in 8,170 g of pure water. Further, 430 g of silicon dioxide (Aerosil 200, manufactured by Nippon Aerosil) was added thereto and dispersed therein to give a binder solution. Separately, 7,400 g of the compound A and 970 g of a low substituted hydroxypropyl cellulose (L-HPC LH-11, manufactured by Shin Etsu Chemical) were mixed in a fluidized bed granulating drier. The binder solution was sprayed onto this mixed powder followed by granulating and drying. The resulting granulated powder was sieved through a 1.9 mm screen. To 249.25 mg of the resulting powder were added crospovidone (Polyplasdone XL-10, manufactured by International Specialty Products) in an amount corresponding to 5.25 mg and sodium stearyl fumarate (PRUV, manufactured by JRS Pharma) in an amount corresponding to 0.5 mg followed by mixing and tableting to give core tablets each weighing 255 mg. Each core tablet was coated with 8 mg of a coating agent to give a film-coated tablet.

Example 18

The compound A (160 g), 20 g of a low substituted hydroxypropyl cellulose (L-HPC LH-B1, manufactured by Shin Etsu Chemical), 10 g of silicon dioxide (Aerosil 200, manufactured by Nippon Aerosil) and 10 g of povidone K30 (Plasdone K29/32, manufactured by International Specialty Products) were mixed in a high-speed stirring granulator (VG-01, manufactured by Powrex Corporation) and pure water was dropped thereinto to granulate. The resulting granulated powder was sieved through a 3.9 mm screen and dried overnight at 40° C. The resulting granulated powder was passed through a sieve having an opening size of 500 μm and sodium stearyl fumarate (PRUV, manufactured by JRS Pharma) in an amount corresponding to 0.2% was added to the resulting powder followed by mixing and tableting to give core tablets each weighing 250.5 mg. The core tablet was coated with 10 mg of a coating agent to give a film-coated tablet.

Example 19

The compound A (5.74 g), 0.13 g of a low substituted hydroxypropyl cellulose (L-HPC LH-11, manufactured by Shin Etsu Chemical) and 0.03 g of silicon dioxide (Aerosil 200, manufactured by Nippon Aerosil) were mixed in a mortar. To this mixed powder was added 0.5 g of a 20% aqueous solution of povidone K30 (Plasdone K29/32, manufactured by International Specialty Products) followed by granulating. The resulting granulated powder was dried overnight at 40° C. The resulting granulated powder was passed through a sieve having an opening size of 500 μm and silicon dioxide (Aerosil 200, manufactured by Nippon Aerosil) in an amount corresponding to 0.5% and sodium stearyl fumarate (PRUV, manufactured by JRS Pharma) in an amount corresponding to 0.2% were added to the resulting powder followed by mixing and tableting to give core tablets each weighing 255 mg.

Comparative Example 1

The compound A (250 mg) was made into a tablet.

Comparative Example 2

The compound A (12 g) was placed in a mortar and 3.2 g of a 20% aqueous solution of povidone K 30 (Plasdone K29/32, manufactured by International Specialty Products) was added thereto followed by granulating. The resulting granulated powder was dried overnight at 40° C. The resulting granulated powder was passed through a sieve having an opening size of 500 μm and sodium stearyl fumarate (PRUV, manufactured by JRS Pharma) in an amount corresponding to 0.5% was added to the resulting powder followed by mixing and tableting to give core tablets each weighing 250 mg.

Comparative Example 3

The compound A (6 g) and 0.34 g of silicon dioxide (Aerosil 200, manufactured by Nippon Aerosil) were mixed in a mortar. To this mixed powder was added 1.65 g of a 20% aqueous solution of povidone K 30 (Plasdone K29/32, manufactured by International Specialty Products) followed by granulating. The resulting granulated powder was dried overnight at 40° C. The resulting granulated powder was passed through a sieve having an opening size of 500 μm and sodium stearyl fumarate (PRUV, manufactured by JRS Pharma) in an amount corresponding to 0.5% was added to the resulting powder followed by mixing and tableting to give core tablets each weighing 250 mg.

Comparative Example 4

The compound A (4 g), 0.25 g of crospovidone (Kollidon CL-SF, manufactured by BASF) and 0.1 g of silicon dioxide (Aerosil 200, manufactured by Nippon Aerosil) were mixed in a mortar. To this mixed powder was added 1.25 g of a 20% aqueous solution of povidone K 30 (Plasdone K29/32, manufactured by International Specialty Products) followed by granulating. The resulting granulated powder was dried overnight at 40° C. The resulting granulated powder was passed through a sieve having an opening size of 500 μm and sodium stearyl fumarate (PRUV, manufactured by JRS Pharma) in an amount corresponding to 0.5% was added to the resulting powder followed by mixing and tableting to give core tablets each weighing 250 mg. The core tablet was coated with 10 mg of a coating agent to give a film-coated tablet.

Comparative Example 5

The compound A (5 g), 0.13 g of carboxymethyl starch sodium (Primojel, manufactured by Matsutani Chemical Industry) and 0.13 g of silicon dioxide (Aerosil 200, manufactured by Nippon Aerosil) were mixed in a mortar. To this mixed powder was added 1.56 g of a 20% aqueous solution of povidone K 30 (Plasdone K29/32, manufactured by International Specialty Products) followed by granulating. The resulting granulated powder was dried overnight at 40° C. The resulting granulated powder was passed through a sieve having an opening size of 500 μm and sodium stearyl fumarate (PRUV, manufactured by JRS Pharma) in an amount corresponding to 0.5% was added to the resulting powder followed by mixing and tableting to give core tablets each weighing 250 mg. The core tablet was coated with 10 mg of a coating agent to give a film-coated tablet.

Industrial Applicability

The tablet of the present invention is a tablet containing (1) the compound A or a salt thereof, (2) a low substituted hydroxypropyl cellulose or croscarmellose sodium and (3) a binder, wherein the amount of the compound A or a salt thereof contained therein is 50 to 95% of the mass of the tablet.

In the tablet of the present invention, the amount of the compound A or a salt thereof contained therein is high, the size is an easily ingestible size, the dissolution property is excellent and the hardness is durable against film coating, packaging and transportation.

The tablet of the present invention is useful as a tablet containing a high amount of the compound A or a salt thereof.

The granulated powder of the present invention is a granulated powder containing (1) the compound A or a salt thereof, (2) a low substituted hydroxypropyl cellulose or croscarmellose sodium and (3) a binder, wherein the amount of the compound A or a salt thereof contained therein is 50 to 95% of the mass of the granulated powder.

The granulated powder of the present invention contains a high amount of the compound A or a salt thereof and is useful as a granulated powder for the manufacture of a tablet containing a high amount of the compound A or a salt thereof.

The invention claimed is:

1. A tablet comprising (1) 50 to 95% of 6-fluoro-3-hydroxy-2-pyrazinecarboxamide or a salt thereof based on the mass of the tablet, (2) a low substituted hydroxypropyl cellulose or croscarmellose sodium, and (3) a binder.

2. The tablet according to claim 1, wherein the low substituted hydroxypropyl cellulose or croscarmellose sodium is a low substituted hydroxypropyl cellulose.

3. The tablet according to claim 1 or 2, wherein the tablet further comprises silicon dioxide.

4. The tablet according to claim 3, comprising 2 to 10% of silicon dioxide based on the mass of the tablet.

5. The tablet according to claim 1, wherein the tablet further comprises a lubricant.

6. The tablet according to claim 5, wherein the lubricant is sodium stearyl fumarate.

7. The tablet according to claim 1, wherein the tablet is made of a granulated powder manufactured by a wet granulation method.

8. The tablet according to claim 1, wherein the tablet is made of a granulated powder manufactured by a fluidized bed granulation method.

9. A granulated powder comprising (1) 50 to 95% of 6-fluoro-3-hydroxy-2-pyrazinecarboxamide or a salt thereof based on the mass of the granulated powder, (2) a low substituted hydroxypropyl cellulose or croscarmellose sodium and (3) a binder.

10. The granulated powder according to claim 9, wherein the low substituted hydroxypropyl cellulose or croscarmellose sodium is a low substituted hydroxypropyl cellulose.

11. The granulated powder according to claim 9 or 10, wherein the powder further comprises silicon dioxide.

12. The granulated powder according to claim 11, comprising from 2 to 10% of silicon dioxide based on the mass of the granulated powder.

13. The granulated powder according to claim 9, wherein the granulated powder further comprises a lubricant.

14. The granulated powder according to claim 13, wherein the lubricant is sodium stearyl fumarate.

15. The granulated powder according to claim 9, wherein the granulated powder is manufactured by a wet granulation method.

16. The granulated powder according to claim 9, wherein the granulated powder is manufactured by a fluidized bed granulation method.

17. The tablet according to claim 1, wherein a content of the low substituted hydroxypropyl cellulose or croscarmellose sodium is from 2 to 20% based on the mass of the tablet.

18. The tablet according to claim 5, wherein a content of the lubricant is from 0.5 to 15% based on the mass of the tablet.

* * * * *